(12) United States Patent
Dadd et al.

(10) Patent No.: US 8,874,240 B2
(45) Date of Patent: Oct. 28, 2014

(54) COCHLEAR IMPLANT ELECTRODE LEAD HAVING A CROSS-SECTION WITH VARIABLE HEIGHT

(75) Inventors: Fysh Dadd, Lane Cove (AU); Claudiu Treaba, Centennial, CO (US); Peter Schuller, Turramurra (AU)

(73) Assignee: Cochlear Limited, Macquarie University, NSW (AU)

( * ) Notice: Subject to any disclaimer, the term of this patent is extended or adjusted under 35 U.S.C. 154(b) by 451 days.

(21) Appl. No.: 13/058,095

(22) PCT Filed: Jul. 8, 2009

(86) PCT No.: PCT/AU2009/000879
§ 371 (c)(1),
(2), (4) Date: Apr. 29, 2011

(87) PCT Pub. No.: WO2010/015017
PCT Pub. Date: Feb. 11, 2010

(65) Prior Publication Data
US 2011/0201997 A1 Aug. 18, 2011

(30) Foreign Application Priority Data
Aug. 8, 2008 (AU) ................................ 2008904063

(51) Int. Cl.
*A61N 1/00* (2006.01)
*A61N 1/05* (2006.01)
*H04R 25/00* (2006.01)

(52) U.S. Cl.
CPC ............ *A61N 1/0541* (2013.01); *H04R 25/606* (2013.01)
USPC ............................................ 607/137; 607/57

(58) Field of Classification Search
CPC .. A61N 1/0541–1/36032; A61F 11/04–11/045
USPC ...................................... 607/137, 55–57, 116
See application file for complete search history.

(56) References Cited

U.S. PATENT DOCUMENTS

| 6,374,143 B1 | 4/2002 | Berrang |
| 7,194,314 B1 | 3/2007 | Richter |
| 7,319,906 B2 * | 1/2008 | Kuzma et al. ................. 607/137 |

FOREIGN PATENT DOCUMENTS

| WO | WO 96/31087 | 10/1996 |
| WO | WO 2010/015017 | 2/2010 |

OTHER PUBLICATIONS

International Search Report for PCT/AU2009/000879, dated Sep. 18, 2009, 4 pages.
Written Opinion for PCT/AU2009/000879, dated Sep. 18, 2009, 6 pages.

* cited by examiner

*Primary Examiner* — Nicholas Lucchesi
*Assistant Examiner* — Melissa A Snyder
(74) *Attorney, Agent, or Firm* — K&L Gates LLP

(57) ABSTRACT

An electrode lead for insertion into a patient's cochlea includes a substantially solid elongate carrier member having lateral and medial sides and opposing transverse surfaces extending between outer surfaces of the lateral and medial sides, wherein the carrier member has a thickness between outer surfaces of the lateral and medial sides, and a plurality of electrodes disposed on or in the medial side. A height of the lateral side between the transverse surfaces is generally greater than a height of the medial side between the transverse surfaces, wherein each of the heights is approximately perpendicular to the thickness.

15 Claims, 8 Drawing Sheets

COCHLEAR IMPLANT ELECTRODE LEAD HAVING A CROSS-SECTION WITH VARIABLE HEIGHT

CROSS-REFERENCE TO RELATED APPLICATIONS

This application is a National Stage Application of International Patent Application No. PCT/AU2009/000879, filed Jul. 8, 2009, which claims the benefit of Australian Provisional Patent Application No. 2008904063, filed on Aug. 8, 2008, the contents of which is hereby incorporated by reference herein.

BACKGROUND

1. Field of the Invention

The present invention is generally directed to cochlear implant electrode leads, and more particularly, to a cochlear implant electrode lead having a cross-section with a variable height.

2. Related Art

A cochlear implant allows for electrical stimulation signals to be applied directly to the auditory nerve fibers of a patient, allowing the brain to perceive a hearing sensation approximating the natural hearing sensation. These stimulation signals are applied by an array of electrodes implanted in the patient's cochlea.

The electrode array is connected to a stimulator unit which generates the stimulation signals for delivery to the electrode array. The stimulator unit in turn is operationally connected to a signal processing unit, which contains a microphone for receiving audio signals from the environment. The signal processing unit processes the audio signals to generate control signals for the stimulator unit.

FIG. 1 shows a diagramatically-representative cross section of a cochlea 50. Shown there are three channels, known as the scala tympani 51, the scala media and the scala vestibuli in use, an electrode lead containing the electrode array is inserted into the scala tympani 51 and caused to make contact with the modiolar wall of the scala tympani 51, close to the ganglion cells within the modiolus.

It is desirable that electrode contacts of the electrode array are positioned as close to the ganglion cells as possible. The spiral ganglion cells lie in the bone or modiolus, adjacent to the inside wall of the scala tympani 51 as shown in FIG. 1. Conventionally, after implantation, the electrode array consisting of electrode contacts should hug the modiolar wall (or inside wall of the scale tympani). When the electrode array is positioned so as to hug the modiolar wall, the electrode contacts are on the medial side of the lead.

In order to facilitate close contact of the electrode contacts of the electrode array, the carrier material forming the electrode lead is molded to assume a specific pre-curved shape having memory. Therefore the natural resting position of the lead has a carved distal lead tip. When the array tip is straightened (for example by stylet or insertion tube), the tip stores elastic energy which exerts a force tending to restore the lead to its originally-molded curved shape. When the lead is implanted, the medial side of the lead hugs the modiolar wail and thus achieves a medial electrode array placement.

SUMMARY

In one aspect of the present invention, an electrode lead for insertion into a patient's cochlea is disclosed. The electrode lead comprises a substantially solid elongate carrier member having lateral and medial sides and opposing transverse surfaces extending between outer surfaces of the lateral and medial sides, wherein the carrier member has a thickness between outer surfaces of the lateral and medial sides, and a plurality of electrodes disposed on or in the medial side. A height of the lateral side between the transverse surfaces is generally greater than a height of the medial side between the transverse surfaces, wherein each of the heights is approximately perpendicular to the thickness.

In another aspect of the present invention, a cochlear implant is disclosed. The cochlear implant comprises a stimulator, and an electrode lead extending from the stimulator and configured for insertion into a patient's cochlea. The electrode lead comprises a substantially solid elongate carrier member having lateral and medial sides and opposing transverse surfaces extending between outer surfaces of the lateral and medial sides, wherein the carrier member has a thickness between outer surfaces of the lateral and medial sides, and a plurality of electrodes disposed on or in the medial side. A height of the lateral side between the transverse surfaces is generally greater than a height of the medial side between the transverse surfaces, wherein each of the heights is approximately perpendicular to the thickness.

In yet another aspect of the invention, a method of forming an electrode lead for insertion into a patient's cochlea is disclosed. The electrode lead comprises a substantially solid elongate carrier member having lateral and medial sides and opposing transverse surfaces extending between outer surfaces of the lateral and medial sides, and having a thickness between outer surfaces of the lateral and medial sides. The method comprises forming a plurality of electrodes commonly connected by a spine, electrically connecting a wire to each of the plurality of electrodes, and disconnecting the spine from the plurality of electrodes to form a sub-assembly. The method further comprises placing the sub-assembly into a cavity of a mold, filling the cavity including the sub-assembly with a polymeric insulating material, and curing the polymeric insulating material around the sub-assembly to form the carrier member having the plurality of electrodes disposed on the medial side and such that a height of the lateral side between the transverse surfaces is generally greater than a height of the medial side between the transverse surfaces, wherein each of the heights is approximately perpendicular to the thickness.

BRIEF DESCRIPTION OF THE DRAWINGS

Embodiments of the present invention will now be described with reference to the accompanying drawings, in which.

DETAILED DESCRIPTION

Certain embodiments of the present invention provide an electrode lead (which may be referred to herein as an electrode array) configured to improve the contact between electrode contacts of the electrode lead and the wall of the cochlea.

Figure 1:
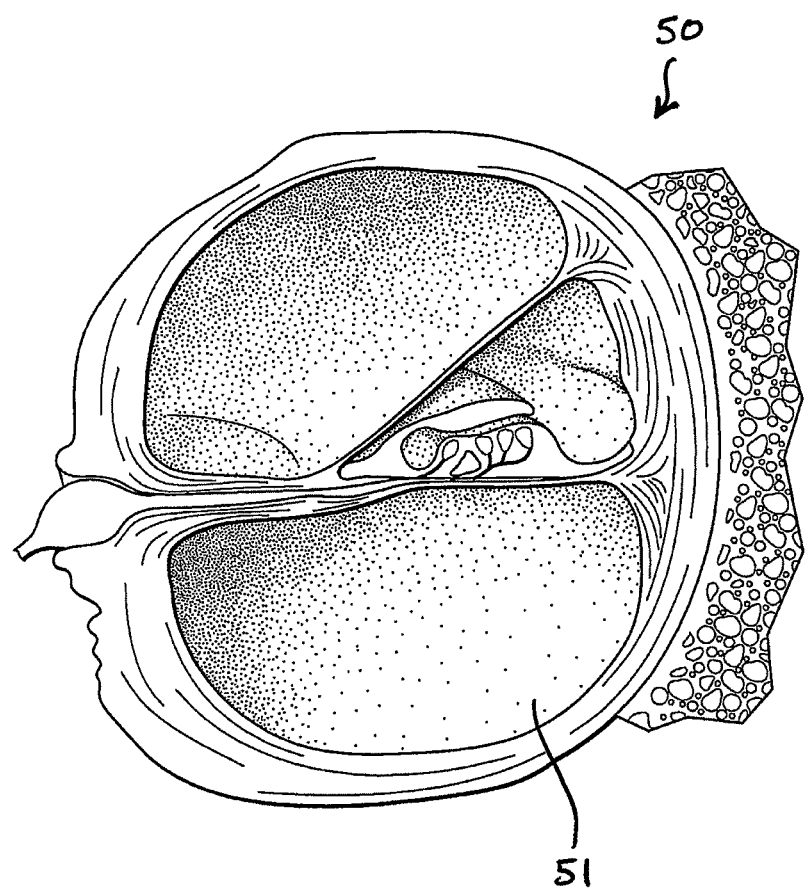
FIG. 1 shows a cross section through a cochlea.
Figure 2:
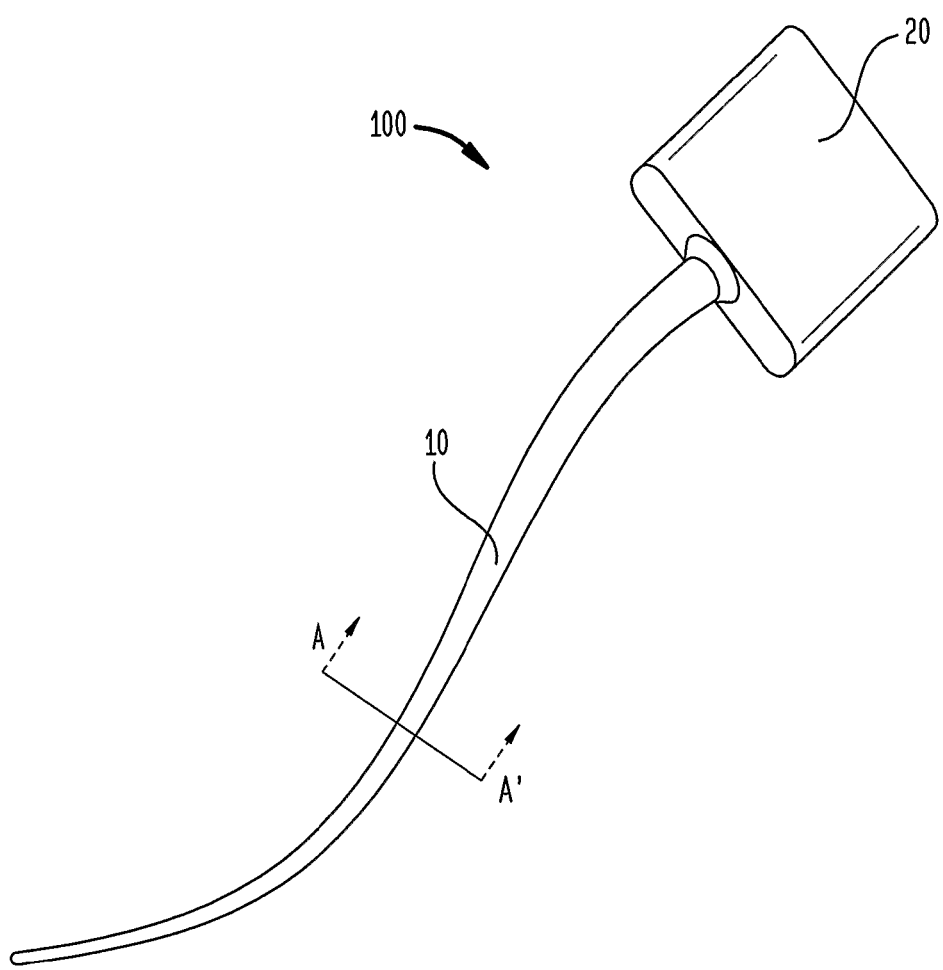
FIG. 2 shows an electrode lead according to embodiments of the present invention.

FIG. 2 shows an exemplary electrode lead 10 extending from a stimulator 20 of a cochlear implant system 100 which, in use, is implanted into a user, in accordance with certain embodiments of the present invention.

Figure 3:
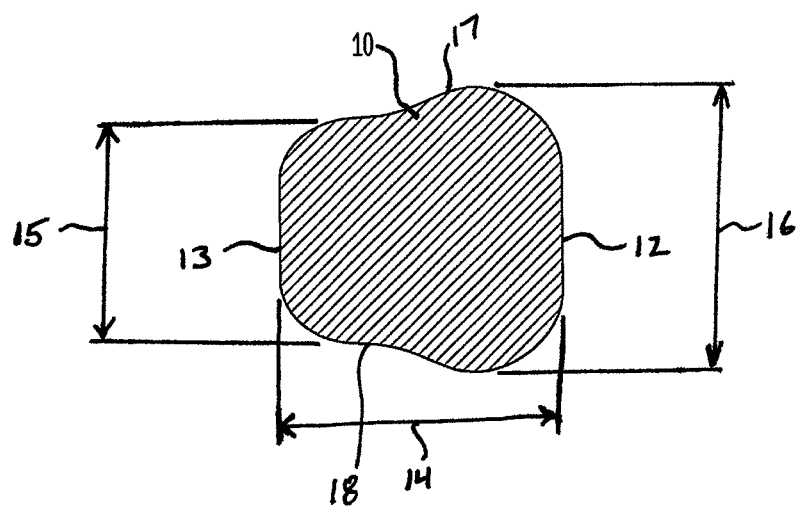
FIG. 3 shows a cross-section along the line A-A' in FIG. 2.

According to some embodiments of the present invention, electrode lead 10 is shaped so as to have a cross-section such that the height of the cross-section is greater at the lateral side than at the medial side. FIG. 3 shows the cross-section of the electrode lead 10 along the line A-A' in FIG. 2. From the perspective of FIG. 2, the right hand side of the cross section is the lateral side 12, and the left hand side is the medial side 13, in one specific form of this, the electrode lead is substantially muffin-shaped, resembling a muffin on its side. Electrode lead 10 also includes surfaces that extend between the outer surfaces of lateral and medial sides 12 and 13, referred to herein as "transverse surfaces." As shown in FIG. 3, electrode lead 10 includes first and second opposing transverse surfaces 17 and 18, each of which extends between the outer surface of lateral and medical sides 12 and 13. As shown in FIG. 3, electrode lead 10 also has a thickness 14. As used herein, the "thickness" of an electrode lead refers to the distance laterally across a cross-section of the lead between the outer surfaces of the lateral and medial sides of the lead. As also shown in FIG. 3, a portion of lateral side 12 has a height 16 and a portion of medial side 13 has a height 15. As used herein, a "height" of an electrode lead refers to a dimension of a cross-section of the lead between opposing transverse surfaces and perpendicular to the thickness of the cross-section.

In the embodiment illustrated in FIG. 3, the cross-section of electrode lead 10 has a generally trapezoidal shape in which the transverse surfaces 17 and 18 are not linear, but instead have a concave portion on the medial side and a convex portion in the lateral side. In addition, lateral side 12 of electrode lead 10 is bulbous such that the portions of the transverse surfaces at lateral side 12 extend beyond the transverse surfaces at medial side 13.

Figure 4:
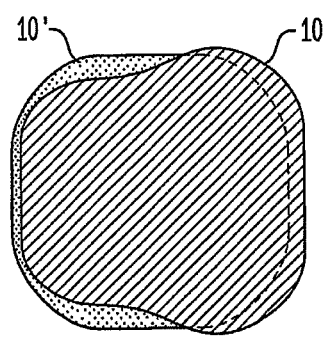
FIG. 4 shows a cross-section of the electrode lead of FIGS. 2 and 3 laid over a cross-section of a conventional electrode lead.

FIG. 4 shows the cross-section of FIG. 3 superimposed over the cross section of a conventional electrode lead 10' as described in U.S. Pat. No. 6,421,569.

Figure 5:
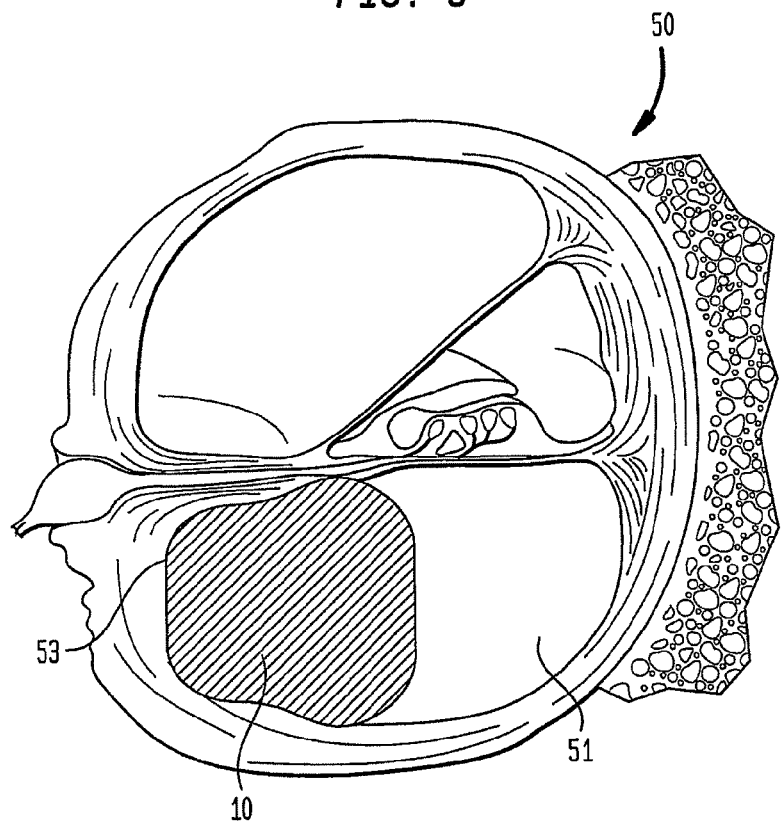
FIG. 5 shows a cross-section of a cochlea with the electrode lead of FIG. 2 inserted therein in accordance with embodiments of the present invention.

FIG. 5 shows a simplified cross section of the cochlea 50. In use, the electrode lead 10 will be positioned such that the medial side contacts the inner wall 53 of the scala tympani 51, close to the spiral ganglion. In some embodiments, the medial side of the electrode lead substantially conforms to the wall of the scala tympani of the cochlea.

Figure 6:
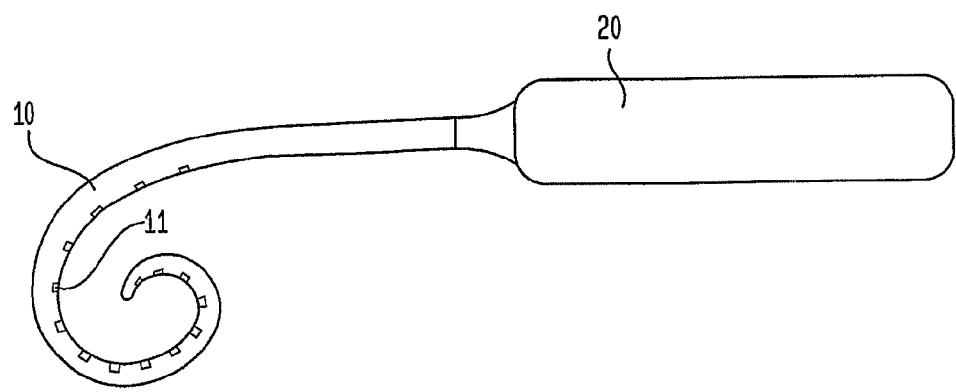
FIG. 6 shows an electrode lead in its curved state in accordance with embodiments of the present invention.

FIG. 6 shows electrode lead 10 in its natural state, in which it is biased into a curved state, with memory to resume that state after temporary straightening during insertion, in accordance with certain embodiments.

Below is a description of one method of forming an electrode lead in accordance with embodiments of the present invention.

An electrode lead in accordance with embodiments of the invention may be formed by a variety of different methods. In some embodiments, forming the electrode lead may include a method of welding of electrode contacts as described in U.S. Pat. No. 6,421,569. An exemplary method may include:
 a) Forming contacts by slicing 0.3 mm wide sections of platinum tube.
 b) Placing the contacts in a welding jig and squashing the contacts into a U shape.
 c) Placing a bundle of 22 wires in the welding jig.
 d) Connecting each wire to a contact (e.g., by welding). (The strand travels from the contact proximally in the bottom of all the proximal U-shaped contacts.)

In some embodiments, forming the electrode lead may also include a method of forming a welded sub-assembly as described in U.S. Pat. No. 6,421,569. An exemplary method may include:
 a) Placing a droplet of silicone in the trough of each electrode contact to secure the wires.
 b) Pressing a production stylet (FIFE coated wire) on top of the strands and silicone in the troughs of the electrode contacts (this stylet is removed later and forms the lumen).
 c) Then, partially filling each electrode trough with more silicone.
 d) Then, placing the sub-assembly in an oven to cure the silicone.
 e) Then, removing the assembly from the straight die.

Figure 7:
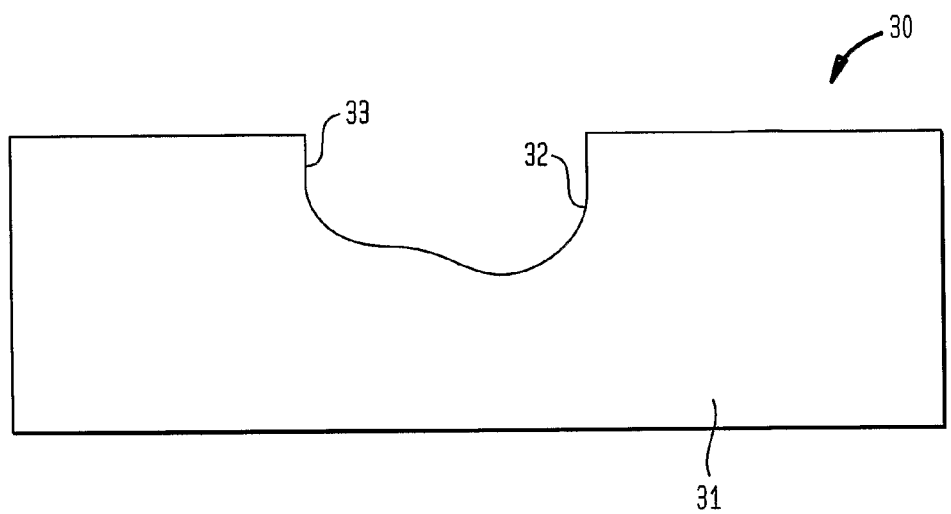
FIG. 7 shows a cross-section of half of a molding die used in forming the electrode lead of FIG. 2.

FIG. 7 shows a portion of a molding die in accordance with certain embodiments of the present invention. This molding die may be used in a variety of different methods. In some embodiments, the die is used in accordance with a method of molding an electrode lead (or array) described in U.S. Pat. No. 6,421,569). The exemplary method may include:
 a) Curving the sub-assembly carefully to match the shape of a curved molding die (described in more detail below with reference to FIG. 7) which will provide the cross-section as described above. The assembly is then placed in the curved molding die with the contacts being located closer to the medial side (inside of the curve).
 b) Packing the space in the die with silicone material.
 c) Placing a matching die cover over the assembly and pressed down the cover.
 d) Then, placing the die in an oven to cure the silicone.
 e) Then, opening the die to allow the resulting electrode array to be removed from the die.

FIG. 7 shows a cross section of one half 31 of a molding die 30 suitable for use in the method described above, in accordance with some embodiments of the present invention. Shown in FIG. 7 is the half-die 31 having a cavity in which the sub-assembly and silicone are placed. As can be seen, the cavity provides a greater height for the electrode lead at one side 32 than at the other side 33. This will provide the molded electrode lead with a cross-section as shown in FIG. 3.

Figure 8:
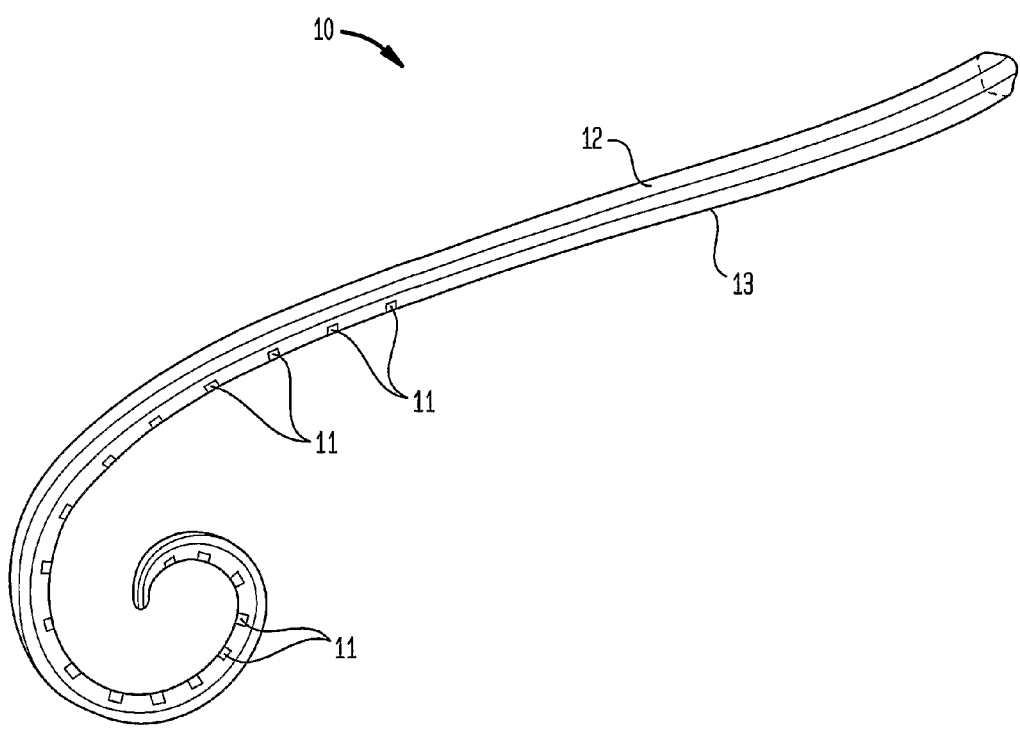
FIG. 8 shows a perspective view of an electrode lead according to embodiments of the present invention.

FIG. 8 shows a perspective view of an electrode lead manufactured by the method described above in accordance with embodiments of the present invention. It can be seen that the precurved electrode lead 10 has a lateral side 12 having a height greater than that of a medial side 13. Electrode contacts 11 are shown disposed in the medial side 13. In some embodiments, the electrode lead is provided as an integral array assembly.

Figure 9:
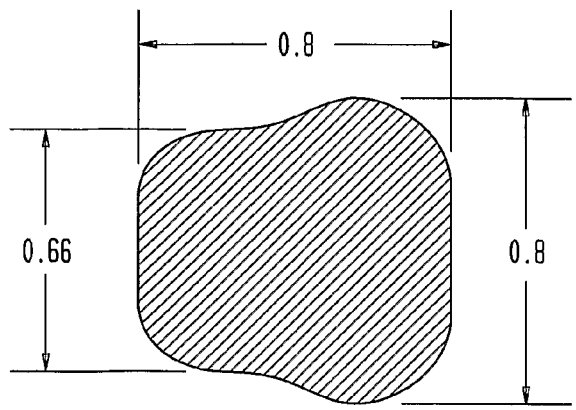
FIG. 9 shows a cross-section of an electrode lead according to embodiments of the present invention including exemplary dimensions.

FIG. 9 shows a cross-section of the electrode lead 10, showing exemplary dimensions in accordance with certain embodiments of the present invention. In this example, the lateral side has a height of about 0.8 mm and the medial side has a height of about 0.66 mm. In some embodiments, these dimensions may range on the lateral side from about 0.5 mm to about 1.2 mm, and on the medial side from about 0.4 to about 0.8 mm. Additionally, as shown in FIG. 9, the portion of the lateral side having a height of about 0.8 mm and the portion of the medial side having a height of about 0.66 mm are approximately equidistant from the center of the cross-section.

Figure 10A:
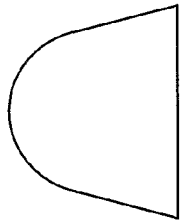
FIGS. 10A to 10E show variations of possible cross-sections of an electrode lead according embodiments of the present invention.
Figure 10B:
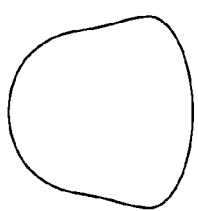
Figure 10C:
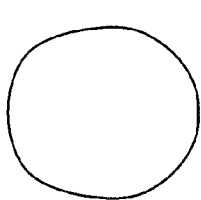
Figure 10D:
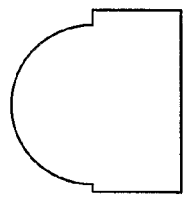
Figure 10E:
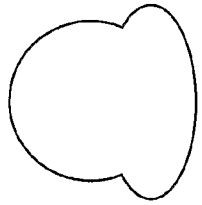

It will also be understood that the "muffin-shape" is but one possible shape, and any other suitable shape may be used in accordance with certain embodiments. FIGS. 10A to 10E show a non-exhaustive range of other possible shapes, in which a height in the cross section of the lateral side is greater than a height in the cross section at the medial side, that may be used in some embodiments instead of the "muffin-shape" as described above. In some of these embodiments, it will be appreciated that the medial side may become the lateral side after about halfway across the cross section. Accordingly, in some embodiments, the maximum height at the lateral side may occur anywhere between the halfway mark of the cross section, to the end of the cross section. Also, as used herein, medial and lateral halves of a cross-section of an electrode lead are respective portions of the cross-section disposed on opposite sides of an axis perpendicular to the thickness and passing through the center of the cross-section. The fourth possible cross-section as shown in FIG. 10D shows the maximum height beginning at the halfway mark and remaining constant until the end of the lateral side. In other cross-sections, the height of the cross-section on the lateral side may reduce towards the end of the cross section on the lateral side after a maximum in the lateral side, such as in FIG. 10B, and in the "muffin shaped" cross-section described above. In other arrangements, as shown in FIG. 10A, the maximum height is at the very end of the cross section on the lateral side.

The present invention has particular advantage when used with an integrated electrode contact assembly, as described in Australian Provisional Patent Application No. 2007906282.

Figure 11:
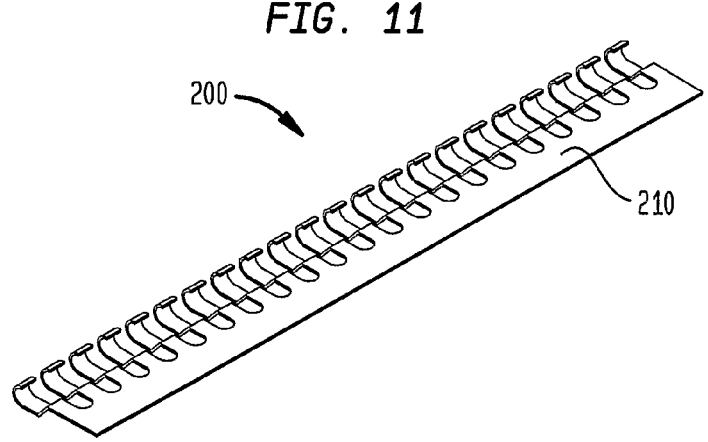
FIG. 11 shows an electrode contact assembly that may be used to form embodiments of the present invention.

In this arrangement, electrode contacts are punched out from a platinum strip into a comb 200 having a spine 210, as shown in FIG. 11, to provide efficiency and support in providing all 22 contacts for an automated welding operation. While it is possible to from a spine with multiple tapers, it is easier for manufacturing to form the spine with a constant taper (or no taper).

With a single taper the electrode array can not match the taper of the scala tympani as the scala tympani has a continuously varying taper as will be appreciated by the person skilled in the art.

Embodiments of the present invention provide an electrode lead (or array) where the carrier portion has a varying taper to align at least more closely with the scala tympani while allowing the electrode contacts to have a single taper. Note that this is a preferred configuration as the basilar membrane is a very delicate structure but is most impacted in modiolus hugging electrode by the lateral half of the electrode.

An electrode lead in accordance with embodiments of the invention may be formed by a variety of different methods. In certain embodiments, forming the electrode lead may include a method of forming a sub-assembly as described in Australian Provisional Patent Application No. 2007906282. An exemplary method may include:

1. Placing a finished comb into a welding jig ready for wires to be joined to the comb. The comb is secured by being held along the length of the spine (a secure hold).
2. Welding a wire to the most proximal electrode contact.
3. Placing a droplet of silicone in the trough of the electrode contact.
4. Welding a second wire to the second most proximal electrode contact.
5. Bedding the wire from the second contact is down into the silicone droplet in the trough of the first electrode.
6. Placing a droplet of silicone in the trough of the second electrode contact.
7. Welding a third and subsequent wires in a similar manner.
8. Placing a production stylet (FIFE coated wire) on top of the wires (this stylet is removed later and forms the lumen).
9. Placing silicone above each contact over the production stylet.
10. Curing the Silicone in an oven.
11. Removing the sub-assembly from the welding jig.
12. Then, cutting the spine off the comb.

As described above, the molding die of FIG. 7 may be used in a variety of different methods. In some embodiments, the die is used in accordance with a method of molding an electrode lead (or array) described in U.S. Pat. No. 6,421,569. An exemplary method may include:

a) Curving the sub-assembly carefully to match the shape of a new curved molding die. The assembly is then placed in the curved molding die with the contacts being located closer to the medial side (inside of the curve).
b) Packing the space in the die with silicone material.
c) Placing a matching die cover over the assembly and pressing the cover down.
d) Then, placing the die in an oven to cure the silicone.
e) Then, opening the die to allow the resulting electrode array to be removed from the die.

The carrier which forms the body of the lead can be made from any suitable material including silicone, polyurethanes or other body compatible polymeric insulating materials. The type and hardness of the insulating carrier can be selected to provide a specific, desired compliance to the lead body in combination with the compliance of the conductor wires and choice of structures incorporated into the lead.

As described above, while the example given refers to electrode contacts with a single taper (or no taper at all), there could also be provided multi-tapering electrode contacts. These could be any number of tapers. Current, prior art designs, have typically three separate tapers, for example near the proximal end there is no taper but a constant width, then a taper, then distally a shallower taper.

It is also possible to have the "muffin" formed with any number of tapers from the intra-cochlea proximal region to the distal region. In certain embodiments, any tapers are transitioned smoothly so that the electrode array is presented as a smooth object into the cochlea.

Any combination of these features is also possible.

The present invention also allows for control of the amount of "pressing force" imparted on the electrode contacts against the wall of the cochlea by controlling the amount of material in the carrier at the lateral side. The more material provided to this region, the greater the curving force provided at that region. This greater curving force provides a greater pressing force to the electrode contacts against the wall of the cochlea. This is particularly useful as any inserted elements such as electrode wires, electrode contacts or support structures will have a natural resistance to curving, and will counteract the curving force provided by the carrier material. In this way, the curving force may be tailored to the particular electrode lead design and may provide different localized curving forces to counter resistance from inserted elements as well as to control the pressing force at discrete regions along, the electrode lead to ensure that the electrode contacts are in contact with the wall of the cochlea regardless of changes or variations in the taper or shape of the scala tympani.

Figure 12:
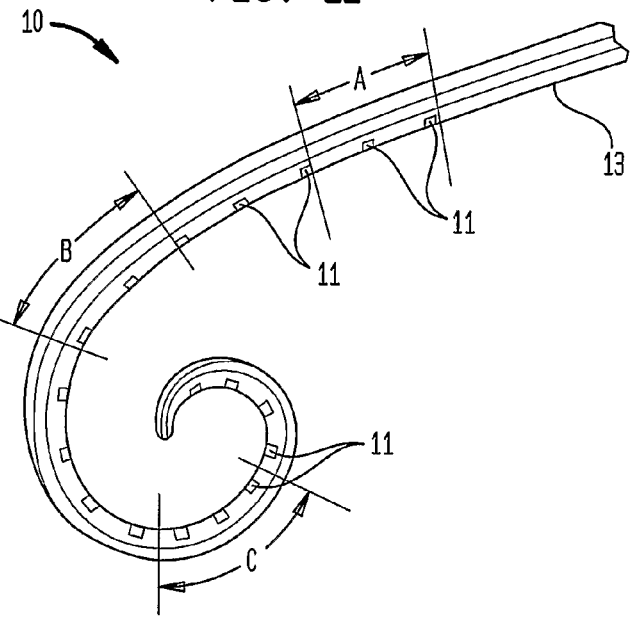
FIG. 12 shows an electrode lead according to embodiments of the present invention with varying dimensions.
Figure 13A:
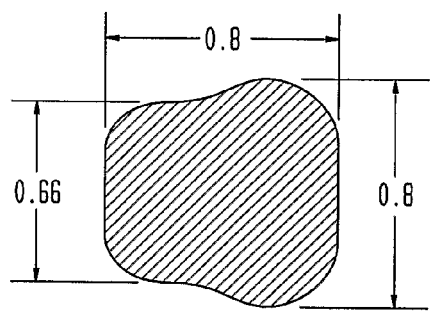
FIGS. 13A to 13C show cross-sections at different points of the electrode lead shown in FIG. 12.
Figure 13B:
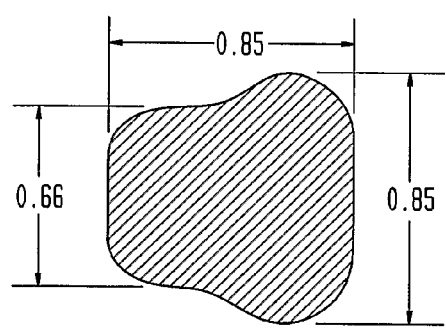
Figure 13C:
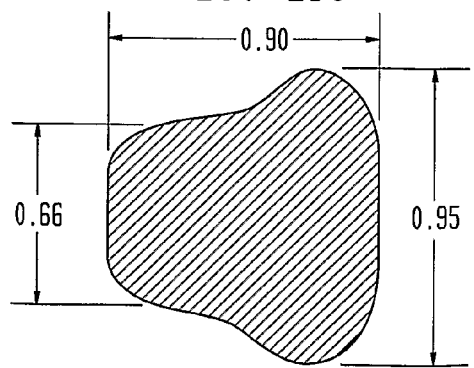

In certain embodiments, an electrode lead is designed to have a variety of different curving forces at different regions along the lead, by varying the amount of material at those regions. In some embodiments, the cross section of the electrode lead varies at least once along the electrode length of the lead so as to vary a curving force along the length of the electrode lead. As shown in FIG. 12, the electrode lead has a first region A having a cross section in the carrier material as shown in FIG. 13A, a second region B having a cross section in the carrier material as shown in FIG. 13B and a third section C having a cross section in the carrier material as shown in FIG. 13C. The regions between these regions may be shaped so as to provide a smooth transition therebetween.

Example dimensions for these figures are shown in Table 1 below. Note that the "slices" are at different intra-cochlear depths, with FIG. 13A being most distal.

TABLE 1

| Dimension | FIG. 13A | 13B | 13C |
| --- | --- | --- | --- |
| Pad height | 0.6 | 0.6 | 0.6 |
| Muffin vertical | 0.65 | 0.7 | 0.8 |
| Muffin horizontal | 0.6 | 0.75 | 0.8 |

In the above examples, it will be noted that the ratio of the vertical and the horizontal height changes depending on the intra-cochlea depth.

The various aspects of certain embodiments of the present invention provide many advantages, such as:

Creating a safer electrode lead. A cross sectional shape that does not fit results in fewer pressure points (both during and after insertion), which can lead to localized or spread damage, particularly in the modiolus and the surrounding hard structures. An electrode lead in accordance with certain embodiments of the present invention may spread any pressure into a larger area and thus be safer.

None of the existing perimodiolar designs match the three-dimensional curved surface of the modiolus. While their inner line is designed to fit that of a mean cochlear model, the electrode lead cross-section was not matched to the curvature of the scala tympani cross-section.

The electrode lead described above in accordance with certain embodiments of the present invention forms the distal end of a lead/array assembly that is adapted to be connected to an implantable cochlear stimulator (ICS) (not shown). The lead/array assembly includes the electrode array, a helix section and a lead end to be connected to the ICS. The ICS is typically housed within a metallic case. The case has an array of feed through terminals corresponding to its multiple channels.

In addition, certain embodiments of the invention provide a method of controlling a pressing force of an electrode lead, having a medial side supporting an electrode array and a lateral side, between one or more electrode contacts of the electrode array and a wall of a cochlea at a particular region, the method comprising controlling an amount of material in the electrode lead in the lateral side at the particular region so as to impart the required pressing force.

The reference to any prior art in this specification is not, and should not be taken as, an acknowledgement of any form of suggestion that such prior art forms part of the common general knowledge.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive.

The invention claimed is:

1. An electrode lead for insertion into a patient's cochlea comprising:
   a substantially solid elongate carrier member having lateral and medial sides and opposing transverse surfaces extending between outer surfaces of the lateral and medial sides, wherein the carrier member has a thickness between outer surfaces of the lateral and medial sides; and
   a plurality of electrodes disposed in the medial side, wherein:
      a height of the lateral side between the transverse surfaces is generally greater than a height of the medial side between the transverse surfaces; and
      the heights of the lateral and medial sides are approximately perpendicular to the thickness of the carrier member.

2. The electrode lead of claim 1, wherein the height of the lateral side is a maximum height of the lateral side and the height of the medial side is a maximum height of the medial side.

3. The electrode lead of claim 1, wherein the height of the lateral side is the height of a first portion of the electrode lead and the height of the medial side is the height of a second portion of the carrier member, wherein the first and second portions are approximately equidistant from the center of the carrier member.

4. The electrode lead of claim 1, wherein the height of the medial side varies along a length of the electrode lead.

5. The electrode lead of claim 4, wherein the height of the medial side is generally greater at a distal end of the electrode lead than at a proximal end of the electrode lead.

6. The electrode lead of claim 4, wherein the height of the lateral side remains substantially constant along the length of the electrode lead.

7. The electrode lead of claim 1, wherein a taper of the electrode lead varies over the length of the electrode lead so as to substantially align with the scala tympani when the electrode lead is inserted into the scala tympani.

8. The electrode lead of claim 1, wherein a cross-sectional shape of the carrier member is generally trapezoidal and each of the transverse surfaces has a concave portion on the medial side and a convex portion on the lateral side.

9. A cochlear implant comprising:
   a stimulator; and
   an electrode lead extending from the stimulator and configured for insertion into a patient's cochlea, the electrode lead comprising:

a substantially solid elongate carrier member having lateral and medial sides and opposing transverse surfaces extending between outer surfaces of the lateral and medial sides, wherein the carrier member has a thickness between outer surfaces of the lateral and medial sides; and a plurality of electrodes disposed in the medial side, wherein:

a height of the lateral side between the transverse surfaces is generally greater than a height of the medial side between the transverse surfaces; and the heights of the lateral and medial sides are approximately perpendicular to the thickness of the carrier member.

10. The cochlear implant of claim 9, wherein a taper of the electrode lead varies over the length of the electrode lead.

11. The cochlear implant of claim 9, wherein the height of the medial side varies along a length of the electrode lead.

12. The cochlear implant of claim 11, wherein the electrode lead is a pre-curved electrode lead having a memory configured to bias the electrode lead into a curved state.

13. The cochlear implant of claim 12, wherein the height of the medial side at a first region of the electrode lead is sufficiently greater than the height of the medial side at a second region of the electrode lead to provide a greater curving force to the electrode lead at the first region than at the second region.

14. The cochlear implant of claim 9, wherein the height of the lateral side is a maximum height of the lateral side and the height of the medial side is a maximum height of the medial side.

15. The cochlear implant of claim 9, wherein the cross-sectional shape of the carrier member is generally trapezoidal and each of the transverse surfaces has a concave portion on the medial side and a convex portion on the lateral side.

* * * * *